United States Patent [19]
Kawano et al.

[11] Patent Number: 6,042,586
[45] Date of Patent: *Mar. 28, 2000

[54] ANTI-CORNEA-COLLAPSING DEVICE FOR OPHTHALMIC SURGERY USING ULTRA-HIGH VACUUM ASPIRATION

[75] Inventors: Koji Kawano, Kagoshima; Hiroyuki Kitsukawa, Tokyo, both of Japan

[73] Assignees: Japan Focus Company Limited; Kawano, Koji, both of Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/027,719

[22] Filed: Feb. 23, 1998

[30] Foreign Application Priority Data

Mar. 6, 1997 [JP] Japan ..................................... 9-067509

[51] Int. Cl.$^7$ ....................................................... A61F 9/00
[52] U.S. Cl. ............................ 606/107; 606/166; 604/19; 604/22; 604/27
[58] Field of Search ..................................... 606/107, 166; 604/35–37, 19, 22, 27, 28, 30, 34; 600/562, 565

[56] References Cited

U.S. PATENT DOCUMENTS 4,516,398  5/1985  Wuchinich ................. 604/22
4,921,477  5/1990  Davis ......................... 604/22
5,167,620  12/1992  Ureche et al. .
5,476,448  12/1995  Urich .

FOREIGN PATENT DOCUMENTS 0312356  4/1989  European Pat. Off. .
4-322715  of 0000  Japan .
1-207059  10/1987  Japan .

Primary Examiner—Michael Buiz
Assistant Examiner—Lien Ngo
Attorney, Agent, or Firm—Staas & Halsey LLP

[57] ABSTRACT

Device for preventing cornea from collapsing including a domed frame with an irrigation duct perforated therein up to the dome of the frame, and elastic latex membrane attached to, and tightly bound at the brim of, the dome; and a chamber formed between the frame and the elastic latex membrane. The frame is incorporated in the irrigation line running from an irrigation bottle to the irrigation inlet of an ultrasound handpiece. Through the irrigation duct perforated in the frame, the chamber is linked to the irrigation line. The chamber inflates or constricts, as irrigation flows in or out, by the inflating and repulsing force of the elastic latex membrane generated by the up-to bottom irrigation. By emitting the irrigation solution into an eye through the irrigation line, the cornea is prevented from collapsing. The device with construction of an elastic latex membrane attached to the domed frame, and incorporated in the irrigation line, is especially useful for ultra-high vacuum phacoemulsification.

8 Claims, 3 Drawing Sheets

ANTI-CORNEA-COLLAPSING DEVICE FOR OPHTHALMIC SURGERY USING ULTRA-HIGH VACUUM ASPIRATION

BACKGROUND OF THE INVENTION

1. Field of the Invention

The present invention relates to an anti-cornea-collapsing device for ophthalmic surgery using the ultra-high vacuum aspiration.

2. Prior Art

It is vitally important to maintain the intraocular pressure (hereinafter referred to as IOP) at an appropriate level during ophthalmic operations by controlling the irrigation and/or aspiration capacity, thus preventing, in particular, cornea from collapsing. The collapse occurs when the system fails to supply sufficient inflow to the eye that compensates for the aspirated amount of liquids and/or tissues, so giving a negative vacuum surge.

Lately, KPE has widely been applied for cataract operations. KPE is the emulsification of opacified nuclei with a needle (ultrasound tip) which is oscillated by a very high frequency ultrasound energy while seizing the nuclei securely with aspiration, thus removing them out of the eye through the needle. The harder the nuclei are, the higher aspiration pressure is need for effective phacofragmentation. In case the aspiration pressure is insufficient, the ultrasound tip often fails to seize the nuclei before they break. Further, the aspiration level at the ultrasound tip starts to rise when the attracted nuclei occlude the tip.

Heretofore, in order to maintain the IOP at an appropriate level during an operation, one method is known that an irrigation bottle is positioned about 65 centimeter high above the patient's eye and then the aspiration capacity is so determined as to meet the irrigation capacity: and according to another method the desired aspiration capacity is first determined and then the height of an irrigation bottle is positioned to meet the aspiration capacity.

Some machines provided for carrying on the latter method into practice are programmed to electrically adjust the height of an irrigation bottle to the desired level to get the appropriate inflow; while several bottles with different heights are incorporated in the identical irrigation line so that one of the irrigation bottles can work to optimize the irrigation capacity by opening its valve and closing other valves.

However, when the highly positioned irrigation bottle is needed to meet the high vacuum aspiration, the irrigating amount and pressure are increased during operation; hence, sometimes it gives pain to the patients.

The Vacuum Surge Suppresser ( hereinafter referred to as VSS) has been disclosed as prior art. It is a silicone-made, domed control valve which is incorporated in the aspiration line—not the irrigation line—between the outlet of the ultrasound handpiece and the aspiration inlet so the valve constricts when the suction pressure rises.

The VSS valve is designed to reduce the outflow by narrowing or blocking the aspiration line which results from collapsing of the VSS valve itself: the said collapsing of the VSS occurs after a sudden rise in the suction pressure in the aspiration line as a result of a nucleus occlusion at the aspiration port of the ultrasound tip. When the nuclei are finally sucked in and the aspiration line is freed from occlusion, the aspiration flow bursts momentarily; hence, without application of the VSS valve, the anterior chamber would collapse.

An invention published under U.S. Pat. No. 1,207,059 has provided a system for irrigation and aspiration, liquid pressures, and flow control. Another invention published under U.S. Pat No. 4,322,715 has provided a system which may optimize the irrigation and aspiration capacity during surgery, works to emulsify, seize and aspirate the nuclei safely and effectively, by selecting one of the preprogrammed parameter-combinations comprising a ultrasound energy level, irrigation bottle height, aspiration flow rate, and preset suction pressure.

As explained above, when the maximum aspiration pressure is preset high enough to improve the effect of phacofragmentation and aspiration, the aspiration pressure rises due to a nucleus occlusion at the aspiration port of the ultrasound tip while at the occlusion break, the aspiration flow bursts momentarily as the aspiration pressure increases. As a consequence, the irrigation capacity turns out insufficient, thereby causing the cornea to collapse.

For the purpose of preventing the cornea from collapsing due to anterior chamber instability the above-referred VSS being incorporated in the aspiration line at the outlet of the ultrasound handpiece, is so designed that its domed silicone valve constricts as the aspiration pressure rises, thereby narrowing or blocking the aspiration line to control the aspiration flow.

However, the silicone-made valve takes a long time to collapse due to the rigidity of silicone: the higher the aspiration pressure is set, the longer time valve takes to reach the desired level. Further, once the valve has collapsed, the aspiration outflow pronouncedly decreases, and it takes some time for the valve to restore to its original shape after collapsing.

Such disadvantages of the VSS system adversely affect the efficiency of continuing nuclei aspiration, and render the system unsuitable for efficient ophthalmic vacuum surgery . Furthermore, since the outflow decreases as the VSS valve collapses, the system fails to aspirate and seize the nuclei effectively, taking longer time for phacoemulsification; that is to say, the VSS is disadvantageous to the extent that the harder the nuclei are, the more ultrasound energy is consumed. The manner in which the VSS valve collapses is not always regular, so the aspiration flow rate can in no way stay even, either.

Heretofore, the prior art has provided either an electric elevator changing the height of the irrigation bottle, or a circulation line system automatically adjusting the amount of irrigation to meet the aspiration pressures and outflows for controlling the IOP. The electric elevator is disadvantageous because if the bottle is positioned high to increase the inflow, the irrigation pressure rises to the extent that patients may feel pains. Higher irrigation pressure causes turbulence inside the eye making it difficult to aspirate the floating nuclei quickly.

These systems usually require functions to store the parameter-combinations of the irrigation and aspiration levels to immediately obtain the desired capacity for stable anterior chamber; thus making the systems electrically and mechanically complicated, incurring high cost of production, and requiring periodical surveillance and maintenance service.

SUMMARY OF THE INVENTION

The device of the invention comprises a domed frame with an irrigation duct perforated therein up to the dome of the frame: an elastic latex membrane attached, and tightly bound at its brim, to the dome: and a chamber to be formed between the frame and the elastic membrane.

Further, the domed frame of the device is incorporated in the irrigation line running from the irrigation bottle to the irrigation inlet of the ultrasound handpiece thereby allowing quick irrigation into the anterior chamber to compensate for the aspirated amount and to remove the cause for anterior chamber instability.

Accordingly, an object of the present invention is to provide an improved anti-cornea-collapsing device for the ultra-high vacuum phacoemulsification which renders easy a continuing nuclei aspiration and phacoemulsification.

Another object of the invention is the provision of an anti-cornea-collapsing device for the ultra-high vacuum phacoemulsification which is suitable for an efficient ophthalmic vacuum surgery.

And another object of the invention is to provide anti-cornea-collapsing device for the ultra-high vacuum phacoemulsification which, as composed of such simple components as a domed frame and elastic latex membrane, can be manufactured at a low cost.

Yet another object of the invention is to provide an anti-cornea-collapsing device for the ultra-high vacuum phacoemulsification which requires no periodical surveillance and maintenance service.

Accordingly, a further object of the invention is to provide an anti-cornea-collapsing device for the ultra-high vacuum phacoemulsification which is economical.

Still a further object of the invention is to provide an anti-cornea-collapsing device for the ultra-high vacuum phacoemulsification which gives little pain to the patient.

Yet still a further object of the invention is to provide an anti-cornea-collapsing device for the ultra-high vacuum phacoemulsification which enables the ultrasound tip to seize the nuclei without fail at the maximum (−) 500 mm Hg aspiration pressure during KPE surgery.

DETAILED DESCRIPTION

FIG. 1 through FIG. 6 illustrate an embodiment of the present invention. The membrane 1 forming part of the device is made of elastic latex, attached, and is tightly bound at its brim 2, to the dome 4 of the frame 3. The elastic latex membrane is designed to be from 0.02 to 0.14 mm thick with a sufficient force to inflate and repulse corresponding to an imbalance of irrigation and aspiration pressure. The membrane preferably has a force to firmly bind the frame at the brim 2.

Figure 1:
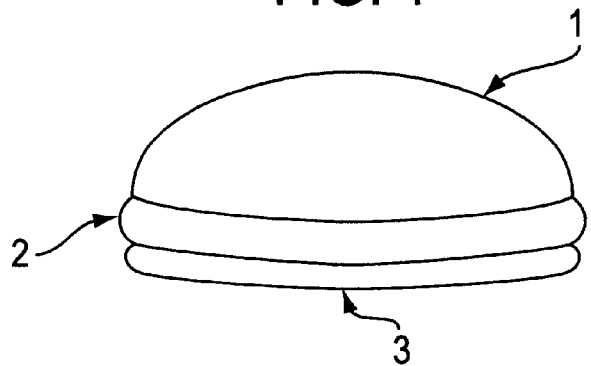
FIG. 1 is a side view of an embodiment of the present invention.
Figure 2:
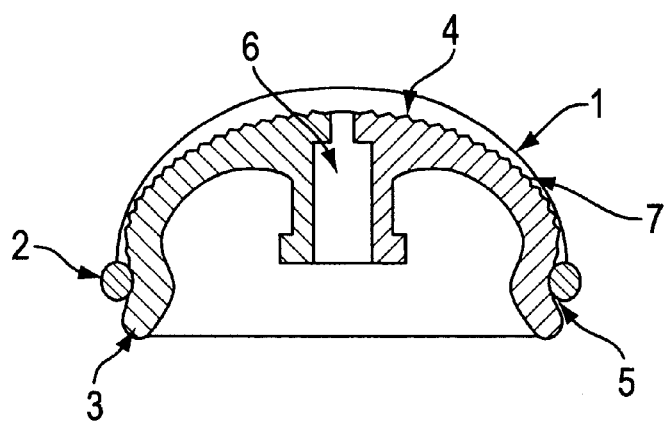
FIG. 2 is a sectional view of FIG. 1.
Figure 3:
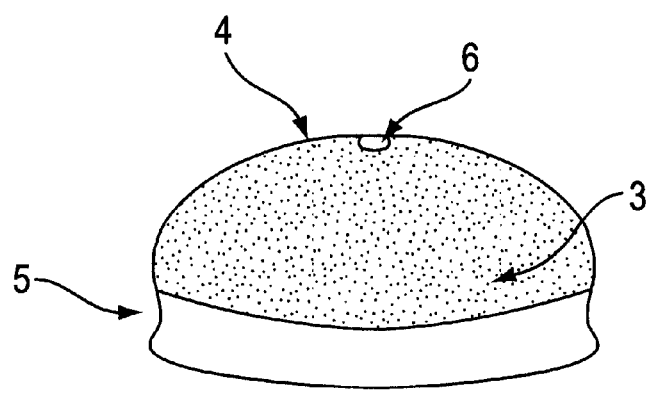
FIG. 3 is a side view of the domed frame.
Figure 4:
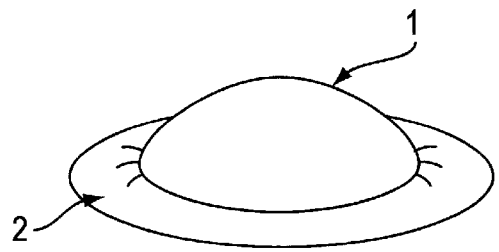
FIG. 4 is a perspective view of the elastic membrane.

As shown in FIG. 3, the device is so designed that the frame 3 is domed: an irrigation duct 6 is perforated through the frame 3 up to the dome 4 as claimed in claim 1 so as to supply water to the chamber 7 to be formed between the frame 3 and the membrane 1. In this case, the frame 3 is preferably very thinly injection-molded to tighten the weight, as shown in FIG. 2.

The latex membrane 1 is bound to the groove 5 formed around the brim of the domed frame 3, using either the tightening force of the said latex membrane 1 or a fixing ring. The surface of the dome 4 of the frame 3 is preferably embossed as shown in FIG. 3, lest the latex membrane 1 should stick to the dome 4 and, therefore, the irrigation solution flows into the chamber 7 through the irrigation duct 6, originating from the irrigation bottle.

Figure 5:
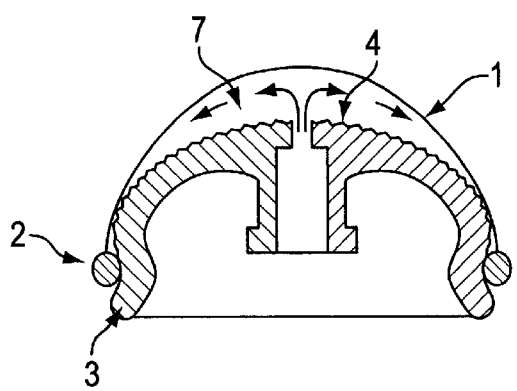
FIG. 5 is a sectional view of the device illustrating the chamber filled up with irrigation solution.

The latex membrane 1 is attached, and bound so tightly at its brim 2, to the dome 4 of the frame 3 that it resists the pressure to be generated by the up-to-bottom irrigation, and the chamber 7 formed between the frame 3 and the membrane 1 may be filled with the irrigation solution as illustrated in FIG. 5.

Figure 6:
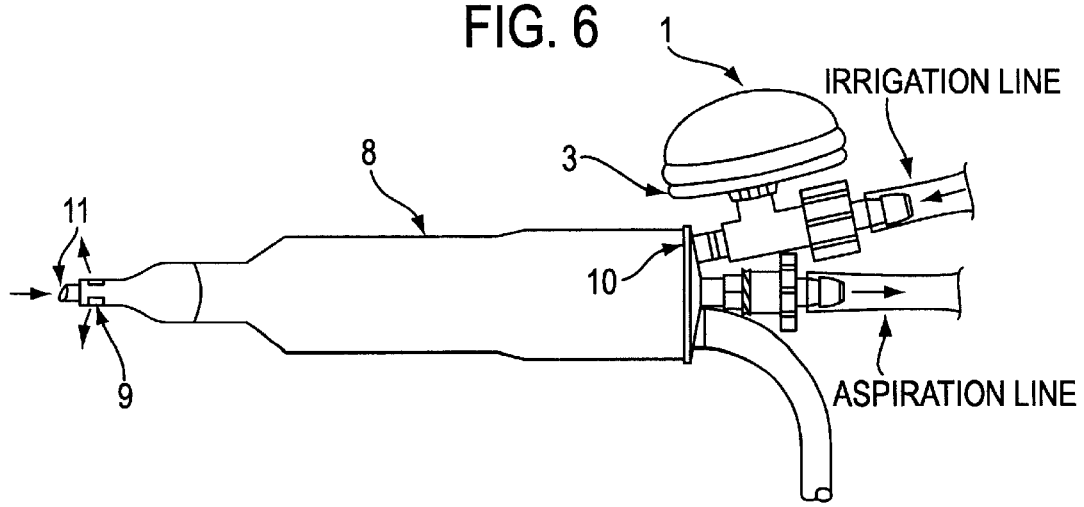
FIG. 6 is a side view of the device connected to the ultrasound handpiece.

With particular reference to FIG. 6, the device is incorporated, by using a connector available in the market, in the irrigation line running from an irrigation bottle to the inlet 10 located at the rear of the ultrasound handpiece 8. The position of incorporating the device in the irrigation line is not specified, but is preferably located close to the irrigation inlet 10.

Figure 7:
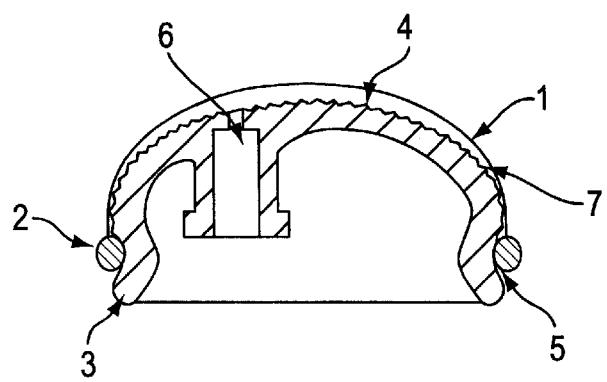
FIG. 7 is a side view of an alternate example of the frame.
Figure 8:
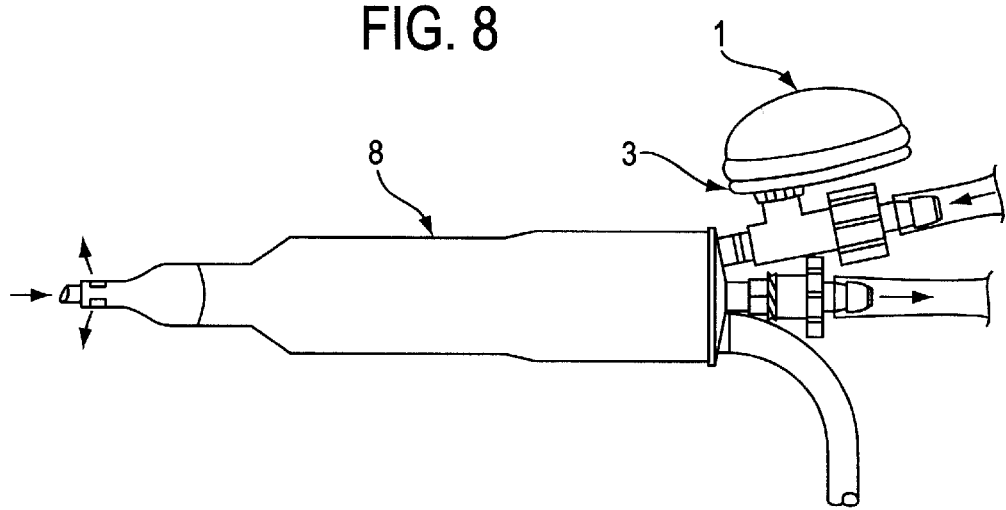
FIG. 8 is a side view of the alternate example of the device connected to the ultrasound handpiece.

FIG. 7 and FIG. 8 illustrate an alternate example of the device. In this example, the irrigation duct 6 is perforated off the center of the dome 4 of the frame 3, or closer to the location of the irrigation inlet 10 at the rear of the ultrasound handpiece 8 for easier manipulation of the handpiece.

Generally, when the ultrasound tip 11 is occluded by the seized nuclei, the aspiration pressure rises: the aspiration outflow bursts momentarily when the nuclei are finally aspirated by the ultrasound tip 11, thus the aspiration line is released from the occlusion. In this case, if the irrigation solution is not supplied sufficiently to fill the anterior chamber, the cornea collapses subsequently.

KPE surgery is executed to remove cataract nuclei in such a manner that the irrigation solution is supplied from the irrigation port 9 of the ultrasound handpiece 8 lest the cornea should collapse, and the emulsified nuclei are aspirated and removed by use of the ultrasound tip 11.

In order to prevent anterior chamber instability as caused by the sudden drop in the volume of anterior chamber during a surgery, it is preferable that the irrigation solution immediately flows into the anterior chamber and fill it automatically to compensate for the momentarily increased aspiration outflow, while the aspiration pressure remains so controlled that the ultrasound tip 11 can firmly seize the nuclei.

The device of the present invention is designed to emit the irrigation solution to fill the anterior chamber automatically and to immediately compensate for the momentarily increased outflow, by making use of the latex membrane 1 with its force to inflate and repulse corresponding to an imbalance of irrigation and aspiration pressures. When the anterior chamber pressure reduces and the aspiration flow rises after nuclei are aspirated by the ultrasound tip 11, the aspiration pressure increases momentarily, as explained above; then the chamber 7 contracts due to the repulsing force of latex membrane 1, thus emitting the irrigation solution into the eye. In this manner, the irrigation solution fills the anterior chamber through the irrigation port 9 so as to immediately compensate for the aspirated volume of the anterior chamber.

With the effect identical with that of moving the irrigation bottle to a higher position, the device is capable of increasing the inflow quickly to the anterior chamber, so maintaining a stable anterior chamber while applying ultra-high vacuum aspiration. Such a capability of applying a ultra-high vacuum aspiration during surgery improves the effect of nuclei aspiration and seizure, and reduces the ultrasound energy required for phacoemulsification of harder nuclei.

Chamber pressure data monitored by a pen recorder indicate that, with application of the device of the present invention, a momentary pressure spike disappears during surgery, suppressing a sudden change of the IOP.

As explained above, the device of the present invention is designed to constrict the chamber 7 by making use of the repulsing force of the latex membrane 1 corresponding to the fall of the pressure in an anterior chamber and to quickly emit the irrigation solution into the anterior chamber so that the chamber 7 is filled with the irrigation solution to compensate for the aspirated volume.

Experimental data evidence that the device prevents cornea from collapsing at a series of clinical evaluations under the preset maximum (−) 500 mm Hg aspiration pressure and 50 cc/min aspiration flow rate.

The device of the present invention enables the ultrasound tip 11 to seize the nuclei without fail at the maximum (−) 500 mm Hg aspiration pressure during KPE surgery.

Further, the device of the present invention may be applicable to ophthalmic surgery other than KPE, and as composed of such simple components as a domed frame and an elastic latex membrane, the device of the present invention can be manufactured at a low cost, thus offering an economical product for sale.

We claim:

1. An anti-cornea-collapsing device to perform phacoemulsification and aspiration using ultra-high vacuum phacoemulsification and better control of irrigation, comprising;

a dome frame having an irrigation duct perforated therein up to a dome of said frame, an elastic latex membrane attached, and tightly bound at its brim, to said dome, and a chamber formed between the frame and the elastic latex membrane.

2. A device as claimed in claim 1 which is incorporated in an irrigation line running from an irrigation bottle to an irrigation inlet of an ultrasound handpiece.

3. A device to prevent cornea collapse during phacoemulsification and aspiration using ultra-high vacuum phacoemulsification, said device comprising:

a domed structure having a passage therein running from an interior surface of said domed structure to an exterior surface of said domed structure; and expansion means for expanding when a fluid flows through said central passage from said interior surface to said exterior surface;

wherein said expansion means is fastened to said domed structure so as to create a chamber between said exterior surface and said expansion means.

4. A device as claimed in claim 3, wherein said expansion means is a latex membrane.

5. A device as claimed in claim 4, wherein said latex membrane includes a brim, and said brim is connected to said domed structure.

6. A device as claimed in claim 3, wherein said passage is formed centrally in said domed structure.

7. A device as claimed in claim 3, wherein said passage is formed off-center in said domed structure.

8. A device as claimed in claim 3, with said device being incorporated in an irrigation line running from an irrigation bottle to an irrigation inlet of an ultrasound handpiece.

* * * * *